United States Patent
Sun et al.

(10) Patent No.: US 8,219,203 B2
(45) Date of Patent: Jul. 10, 2012

(54) COCHLEAR IMPLANT UTILIZING MULTIPLE-RESOLUTION CURRENT SOURCES AND FLEXIBLE DATA ENCODING

(75) Inventors: Xiaoan Sun, Irvine, CA (US); Hongbin Chen, Irvine, CA (US)

(73) Assignee: Nurotron Biotechnology, Inc., Irvine, CA (US)

( * ) Notice: Subject to any disclaimer, the term of this patent is extended or adjusted under 35 U.S.C. 154(b) by 0 days.

(21) Appl. No.: 13/312,659

(22) Filed: Dec. 6, 2011

(65) Prior Publication Data
US 2012/0083859 A1   Apr. 5, 2012

Related U.S. Application Data

(63) Continuation of application No. 11/779,216, filed on Jul. 17, 2007, now abandoned.

(51) Int. Cl.
*A61N 1/36* (2006.01)

(52) U.S. Cl. ............... 607/57; 607/55; 607/56; 607/137

(58) Field of Classification Search .............. 607/55–57, 607/137
See application file for complete search history.

*Primary Examiner* — Niketa Patel
*Assistant Examiner* — Rex R Holmes
(74) *Attorney, Agent, or Firm* — Crowell & Moring LLP

(57) ABSTRACT

A programmable cochlear implant system utilizes multiple-resolution current sources and flexible data-encoding scheme for transcutaneous transmission. In certain embodiments, the number of current sources may be equal to or greater than 2, but equal or less than N−1, where N is the number of electrodes. The multi-resolution current source may introduce offset currents to achieve perceptually-based multiple resolutions with high resolution at low amplitudes and low resolution at high amplitudes. The flexible data-encoding scheme may allow arbitrary waveforms in terms of phase polarity, phase duration, pseudo-analog-waveform, while producing high-rate and high-temporal-precision stimulation. In one embodiment, a 2-current-source system may support simultaneous and non-simultaneous stimulation as well as monopolar, bipolar, pseudo-tripolar, and tripolar electrode configurations.

22 Claims, 19 Drawing Sheets

| 1-2 | 3-7 | 8-16 |
|---|---|---|
| 00 | 00001 | xxxxxxxx |

510:

| | Electrode1 (5) | FirstPh1 (1) | SecondPh1 (1) | Amplitude1 (8) | Parity1 (1) | PhWidth (10) | PhGap (5) | Parity (1) |
|---|---|---|---|---|---|---|---|---|
| F | 00001 | 0 | 1 | xxxxxxxx | x | xxxxxxxxxx | xxxxx | x |
| | Electrode2 (5) | FirstPh2 (1) | SecondPh2 (1) | Amplitude2 (8) | Parity2 (1) | | | |
| | 00000 | x | x | xxxxxxxx | x | | | |

| 1-2 | 3-7 | 8-16 |
|-----|-------|----------|
| 00 | 11101 | xxxxxxxx |

530

| | Electrode1 (5) | FirstPh1 (1) | SecondPh1 (1) | Amplitude1 (8) | Parity1 (1) |
|---|---|---|---|---|---|
| 1 | 00001 | 0 | 1 | xxxxxxxx | x |
| | Electrode2 (5) | FirstPh2 (1) | SecondPh2 (1) | Amplitude2 (8) | Parity2 (1) |
| | 00011 | 1 | 0 | xxxxxxxx | x |

| PhWidth (10) | PhGap (5) | Parity (1) |
|---|---|---|
| xxxxxxxxxx | xxxxx | x |

| 1-2 | 3-7 | 8-16 |
|---|---|---|
| 00 | 11011 | xxxxxxxxx |

550

| Electrode1 (5) | FirstPh1 (1) | SecondPh1 (1) | Amplitude1 (8) | Parity1 (1) | | |
|---|---|---|---|---|---|---|
| 00001 | 0 | 1 | xxxxxxxx | x | | |
| Electrode2 (5) | FirstPh2 (1) | SecondPh2 (1) | Amplitude2 (8) | Parity2 (1) | PhWidth (10) | PhGap (5) | Parity (1) |
| 00000 | x | x | xxxxxxxx | x | xxxxxxxxxx | xxxxx | x |

FIG. 5D

| 1-2 | 3-7 | 8-16 |
|---|---|---|
| 00 | 11101 | xxxxxxxxx |

560

| | Electrode1 (5) | FirstPh1 (1) | SecondPh1 (1) | Amplitude1 (8) | Parity1 (1) | | |
|---|---|---|---|---|---|---|---|
| 1 | 00001 | 0 | 1 | xxxxxxxx | x | | |
| | Electrode2 (5) | FirstPh2 (1) | SecondPh2 (1) | Amplitude2 (8) | Parity2 (1) | | |
| | 00000 | x | x | xxxxxxxx | x | | |
| | | | | PhWid (10) | PhGap (5) | Par (1) |
| | | | | xxxxxxxxxx | xxxxx | x |

| 1-2 | 3-7 | 8-16 |
|---|---|---|
| 00 | 11111 | xxxxxxxxx |

580

| | Electrode1 (5) | FirstPh1 (1) | SecondPh1 (1) | Amplitude1 (8) | Parity1 (1) | | |
|---|---|---|---|---|---|---|---|
| 1 | 00010 | x | x | ½ of amplitude | x | | |
| | Electrode2 (5) | FirstPh2 (1) | SecondPh2 (1) | Amplitude2 (8) | Parity2 (1) | PhWidth (10) | PhGap (5) | Parity (1) |
| | 00010 | x | x | ½ of amplitude | x | xxxxxxxxxx | xxxxx | x |

| Frame Start (2) | Electrode1 (5) | FirstPh1 (1) | SecondPh1 (1) | Amplitude1 (8) | Parity1 (1) |
|---|---|---|---|---|---|

595

Bits 1-2:   2 bits, start of a data frame.

Bits 3-7:   5 bits electrode info for the applied current source

Bit 8:      1 bit sign info of first phase of pulse, "0" negative, "1" positive.

Bit 9:      1 bit sign info of second phase of pulse, "0" negative, "1" positive.

Bits 10-17: 8 bits amplitude info of a pulse.

Bit 18:     1 bit parity check for pulse info, bits 3-17.

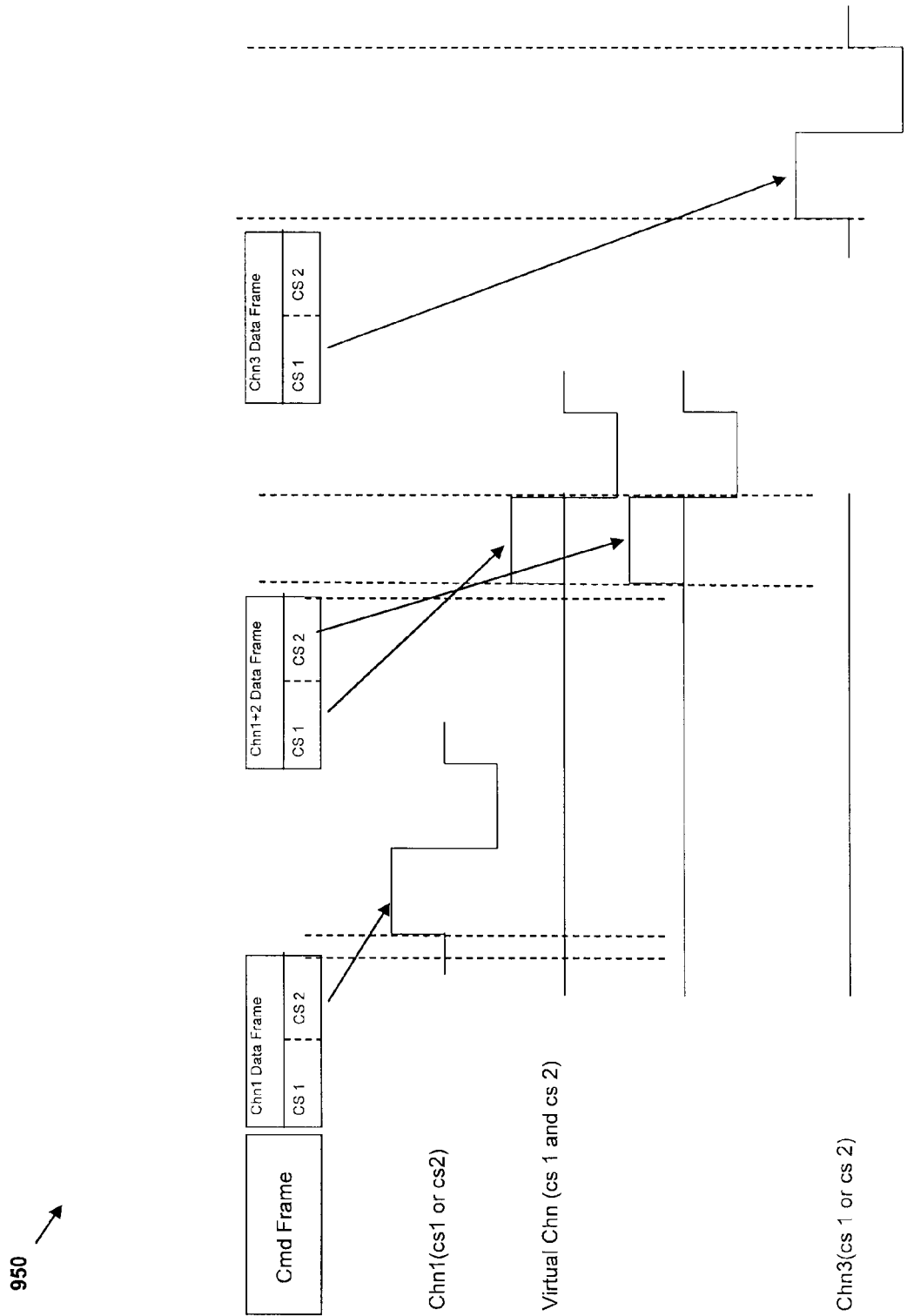

COCHLEAR IMPLANT UTILIZING MULTIPLE-RESOLUTION CURRENT SOURCES AND FLEXIBLE DATA ENCODING

CROSS REFERENCE TO RELATED APPLICATION

This application is a continuation of application Ser. No. 11/779,216, filed Jul. 17, 2007.

FIELD OF THE INVENTION

The present invention relates to an implanted auditory prosthesis that utilizes multiple-resolution current sources and a data encoding scheme.

BACKGROUND

Cochlear implants are electronic medical device to help deaf or severely-hearing-impaired people. They typically consist of an external signal processor, a transmission coil, an implantable package with a receiver coil, a hermetically sealed circuit, and an electrode array. More particularly, these systems include a microphone to receive sounds and convert them into corresponding electrical signals. These electrical signals may then be processed to generate a series of stimulation pulses that are delivered to the inner ear using a series of implanted electrodes. The stimulation of these implanted electrodes allows the implantee to perceive the corresponding ambient sounds.

A typical cochlear implant includes both an external component and an internal component. The external component will typically include a microphone, a speech processor, and a radio-frequency transmitter, while the internal component includes an implanted receiver, a hermetically-sealed decoding circuit, and a series of implanted electrodes. However, there are also numerous other designs currently available. Regardless of the specific configuration, a basic premise of all cochlear implant devices is that ambient sounds are detected by the microphone and a transduced signal representative of this signal is then generated. The transduced signal is then processed by a speech processor in accordance with one of several possible strategies.

One of the primary design considerations for cochlear implants is the current source design. To that end, there are two primary types of current source designs currently in use. The first is to use one current source for all N electrodes, while the second approach is to use N current sources for N electrodes. Some products even use 2N current sources for N electrodes for more flexibility. Each solution has its own advantages and disadvantages. For example, with one current source for all electrodes, the size, complexity, and power consumption of current stimulator are low. But the stimulation mode is also restricted by the ability of one current source. No simultaneous stimulation, current steering, or multi-polar stimulation strategies are supported. For N (or 2N) current sources for N electrodes, more flexibility and functionality of stimulation are achieved at the expense of size, complexity, and power consumption.

Current resolution is an important factor for current source design, especially for low stimulation level. For cochlear implant users, the ratio of current variation versus current $\Delta I/I$ is more important than the current variation $\Delta I$ itself. Traditional linear step-size current source uses a constant $\Delta I$. Therefore, at low stimulation level where I is small, $\Delta I/I$ is large. To lower $\Delta I/I$, one solution is to increase the number of current amplitude bit. However, this results in an increase in the number of current sources in the internal circuit and lowers the stimulation rate (8-bit requires 256 unit current sources and 10-bit requires 1024 unit current sources). When the stimulation level is close to the most comfortable loudness (MCL) and the value I is large, $\Delta I/I$ is usually too small and the resolution space is wasted. As such, there is a need for an improved cochlear implant which provides a more balanced solution for both complexity and functionality.

BRIEF SUMMARY OF THE INVENTION

Disclosed and claimed herein is a programmable cochlear implant that utilizes multiple current sources and a flexible data-encoding scheme. In one embodiment of the invention, a method for stimulating electrodes implanted in a human inner ear includes the acts of multiplexing current sources in accordance with a stimulation mode set using a command frame, and encoding stimulation data for the stimulation of the plurality of electrodes in a data frame following the command frame, where the stimulation data include electrode address information, phase polarity information and amplitude information. The method further includes generating a stimulation pulse based on the stimulation data and using one or more of the current sources in accordance with the stimulation mode, and delivering the stimulation pulse to the electrodes in accordance with the stimulation data.

Other aspects, features, and techniques of the invention will be apparent to one skilled in the relevant art in view of the following detailed description of the invention.

BRIEF DESCRIPTION OF THE DRAWINGS

FIG. 2B is one embodiment of a scheme of self-timing with pulse-width-modulation bit coding;

FIGS. 5A-5F depict embodiments of command and data frames for various stimulation modes in accordance with the principles of the invention;

FIGS. 9A-9C illustrate various continuous-interleaved-sampling strategy (CIS) implementations in accordance with one or more embodiments of the invention.

DETAILED DESCRIPTION OF EXEMPLARY EMBODIMENTS

Figure 1:
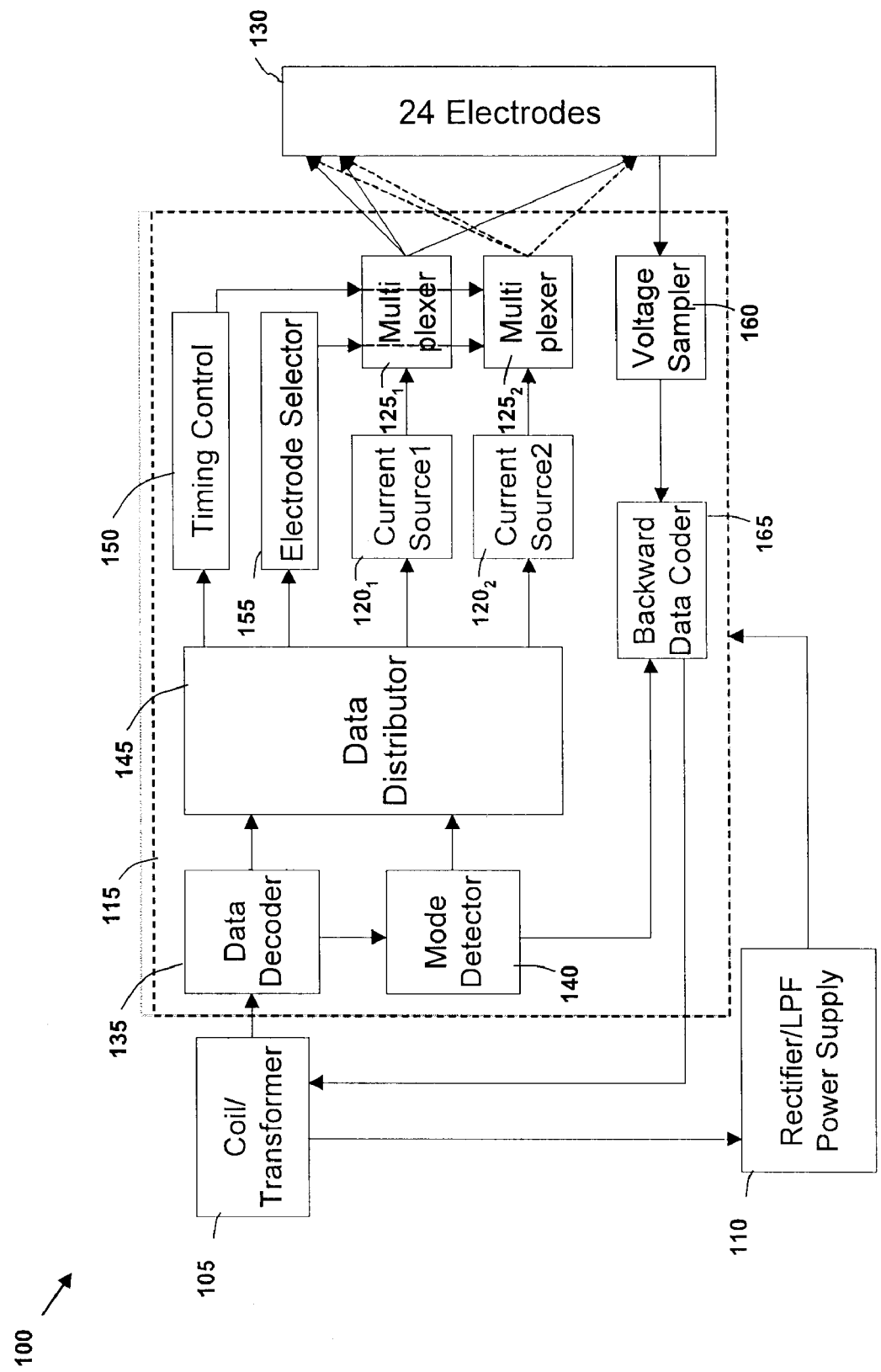
FIG. 1 is a block diagram of one embodiment of a cochlear prosthesis in which two current sources are utilized.

Described and claimed herein is a programmable cochlear implant system utilizing multiple-resolution current sources and a flexible data-encoding scheme. In one embodiment, the system can support simultaneous and non-simultaneous stimulation as well as monopolar, bipolar, pseudo-tripolar, and tripolar electrode configurations.

One aspect of the invention is a cochlear implant having 2 to N−1 current sources for N electrodes. In one embodiment, the number of amplitude bits are balanced with the current resolution at a low stimulation level. By introducing an offset current circuit consisting of three current sources whose states are controlled by 2-bit range information, a four-range current source may be implemented with four different current resolutions of I, 2I, 4I, and 8I, where I is the minimum reference current. Compared with traditional single range current source, this embodiment improves current resolution by 4 times at low stimulation level, according to one embodiment. In another embodiment, the invention provides high resolution by not overlapping resolution space among different ranges.

Another aspect of the invention is a highly-flexible data encoding scheme to support the aforementioned design of 2 to N−1 current sources. The information for each current source may be modularized and conveniently added or removed from a data frame. With each module, the phase polarity, amplitude, stimulating electrode, and phase duration of electrical stimulation can be individually set for each current source. Therefore, flexible stimulation modes, stimulation strategies, arbitrary pulse polarity, arbitrary stimulation waveforms, flexible pulse duration and inter-phase gap may all be supported. In one embodiment, the range of pulse widths may be from 1 μs to 1024 μs. Similarly, the range of inter-phase gap may be from 0 μs to 31 μs. In one embodiment, the resolution for both may be essentially 1 μs. Finally, a high-rate stimulation mode is supported by a special command specifying only one pulse duration, producing a 31-kHz overall stimulation rate with 1 current source and a 62-kHz rate with 2 current sources.

The timing control for implanted circuit may be an important factor for the normal operation of a current stimulator. While one solution has been to add a local timer in the implanted circuit, this tends to increase the power consumption and lower the reliability of the circuit. Moreover, any minor defect of the timer will cause unpredictable error in the internal circuit and current stimulator. Also, it is very difficult to synchronize the timing between external timer and internal timer. To achieve a reliable synchronization between the two timers, usually a phase lock loop (PLL) circuit is required in the implanted circuit, which itself is complicated and power hungry. Thus, another aspect of the invention is to provide timing from outside such that no timer or PLL circuit is required inside. As will be described in more detail below, with a careful design of bit coding which enables signal level changes at the beginning of each data bit, this data encoding scheme can provide timing information to the implanted circuit, in addition to providing power and data.

Referring first to FIG. 1, depicted is one embodiment of a cochlear prosthesis 100 configured to implement one or more embodiments of the invention. As shown, the cochlear prosthesis 100 includes a cool/transformer 105 coupled to a rectifier/LPF power supply 110 and a processing circuit 115. In one embodiment, the power supply 110 is itself electrically coupled to the processing circuit 115, as shown in FIG. 1.

While in the embodiment of FIG. 1 processing circuit 115 includes two current sources $120_1$ and $120_2$, it should equally be appreciated that additional current sources may similarly be included. As shown, current sources $120_1$ and $120_2$, are each coupled to multiplexers $125_1$ and $125_2$, respectively. In turn, multiplexers $125_1$ and $125_2$ may provide current signals to a plurality of electrodes 130, in accordance with a selected stimulation mode. While 24 electrodes are depicted in FIG. 1, it should equally be appreciated that more or fewer electrodes may be included with the cochlear prosthesis 100 of FIG. 1.

Processing circuit 115 is further depicted as including a data decoder 135 for decoding the incoming data, and mode detector 140 for detecting the mode of the incoming data.

Once the data is decoded and the mode detected, the data distributor 145 may use this information to control the current sources $120_1$ and $120_2$, timing control 150 and electrode selector 155, as shown in FIG. 1. As shown, the timing control 150 and electrode selector may be used to selectively stimulate one or more of the plurality of electrodes 130 using one or both of the current sources $120_1$ and $120_2$. The processing circuit 115 may further comprise a voltage sampler 160 and backward data coder 165 for transmitting information regarding electrode impedance, electrical field potentials, current flow through the internal receiving coil, data decoding status, and evoked neural activities. It should be understood that, with the exception of the plurality of electrodes 130, the other components of the cochlear prosthesis 100 may comprise an external portion, meaning that such components may not be implanted under the skin or residing within the inner ear.

With the 2-current-source configuration of FIG. 1 and a highly-flexible data encoding scheme as described herein, a large variety of stimulation modes and strategies may be implemented. If only one current source were used, only standard mono-polar or bipolar CIS stimulation pulses can be generated. By using two current sources simultaneously (e.g., current sources $120_1$ and $120_2$), traditional non-overlapping CIS, as well as overlapping CIS (virtual channel) and even alternating monophasic CIS are enabled.

Figure 2A:
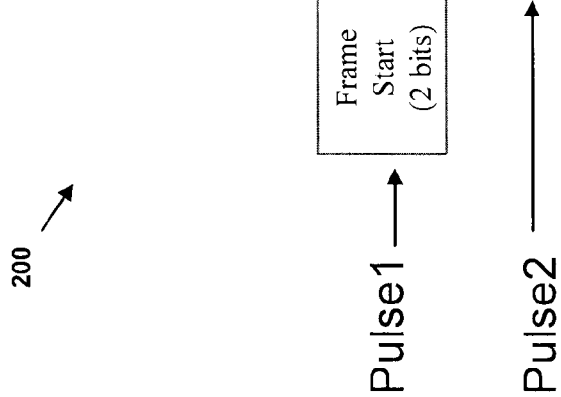
FIG. 2A is the data encoding format supporting from two current sources in accordance with one embodiment.

Referring now to FIG. 2A, depicted is one embodiment of a data frame 200 comprised of a total of 50 bits. In the depicted embodiment, the individual bits include:

Bits 1-2: 2 bits, start of a data frame.
Bits 3-7: 5 bits electrode info for current source 1, named Pulse1.
Bit 8: 1 bit sign info of first phase of Pulse1, "0" negative, "1" positive.
Bit 9: 1 bit sign info of second phase of Pulse1 "0" negative, "1" positive.
Bits 10-17: 8 bits amplitude info of Pulse1.
Bit 18: 1 bit parity check for Pulse1 info, bits 3-17.
Bits 19-23: 5 bits electrode info for next pulse of current source 2, named Pulse2.
Bit 24: 1 bit sign info of first phase of Pulse2, "0" negative, "1" positive.
Bit 25: 1 bit sign info of second phase of Pulse2, "0" negative, "1" positive.
Bits 26-33: 8 bits amplitude info of Pulse2.
Bit 34: 1 bit parity check for Pulse2 info, bits 19-33.
Bits 35-44: 10 bits phase width.
Bits 45-49: 5 bits inter-phase gap.
Bit 50: 1 bit parity check for phase info, bits 35-49.

The bit coding of the proposed data encoding scheme may be used to provide timing control for internal pulse generation. In this way, the implanted circuit may not require a local timer. After electrode and amplitude information are provided in the beginning of a data frame, the remaining bits in a data frame (e.g., data frame 200) provide pulse width and inter-phase gap information and may also act as clock signal for the timing control of current pulse. Phase extending bits can be added after a data frame to generate long phase duration pulses. The start and end of each phase of a pulse may be synchronized by the onset of bits in a data frame. In one embodiment, each bit may include of 10 to 15 RF cycles to provide cycle error tolerance. It should be appreciated that the proposed timing control may make the implanted circuit more reliable and easier to implement.

As previously mentioned, one embodiment of the coding scheme may support flexible 2 to N−1 current sources for N electrodes. For each current source, one embodiment of the coding scheme has 16 bits in date frame 200 corresponding to it, including 5-bit electrode address information, 2-bit phase polarity information and 8-bit pulse amplitude information, and 1 parity check bit. In this fashion, multiplexing of 2 or more current sources to achieve monopolar, bipolar, and pseudo-tripolar stimulation modes is enabled. The pseudo-tripolar refers to apically or basally applied negative current to sharpen the electric field. A true tripolar will sharpen the field from both sides. In certain embodiments, alternating mono-phasic stimulus may result in the power consumption being at least as good as regular bipolar stimulation. In addition, with 3 or more current sources true tripolar stimulation may be provided.

It should further be appreciated that multiplexing 2 or more current sources may achieve both simultaneous and non-simultaneous virtual channels. To that end, in one embodiment the total number of virtual channel may be at least N+(N−1), where N is the number of electrodes.

In certain embodiments, a pulse (e.g., Pulse1, Pulse2) always starts and finishes within one data frame. After electrode, amplitude and phase polarity information are provided, the width and phase gap bits in a data frame may act as a clock signal for the timing control of present pulse. The start and end of each phase of a pulse may be synchronized by the onset of bits in a data frame.

Figure 2B:
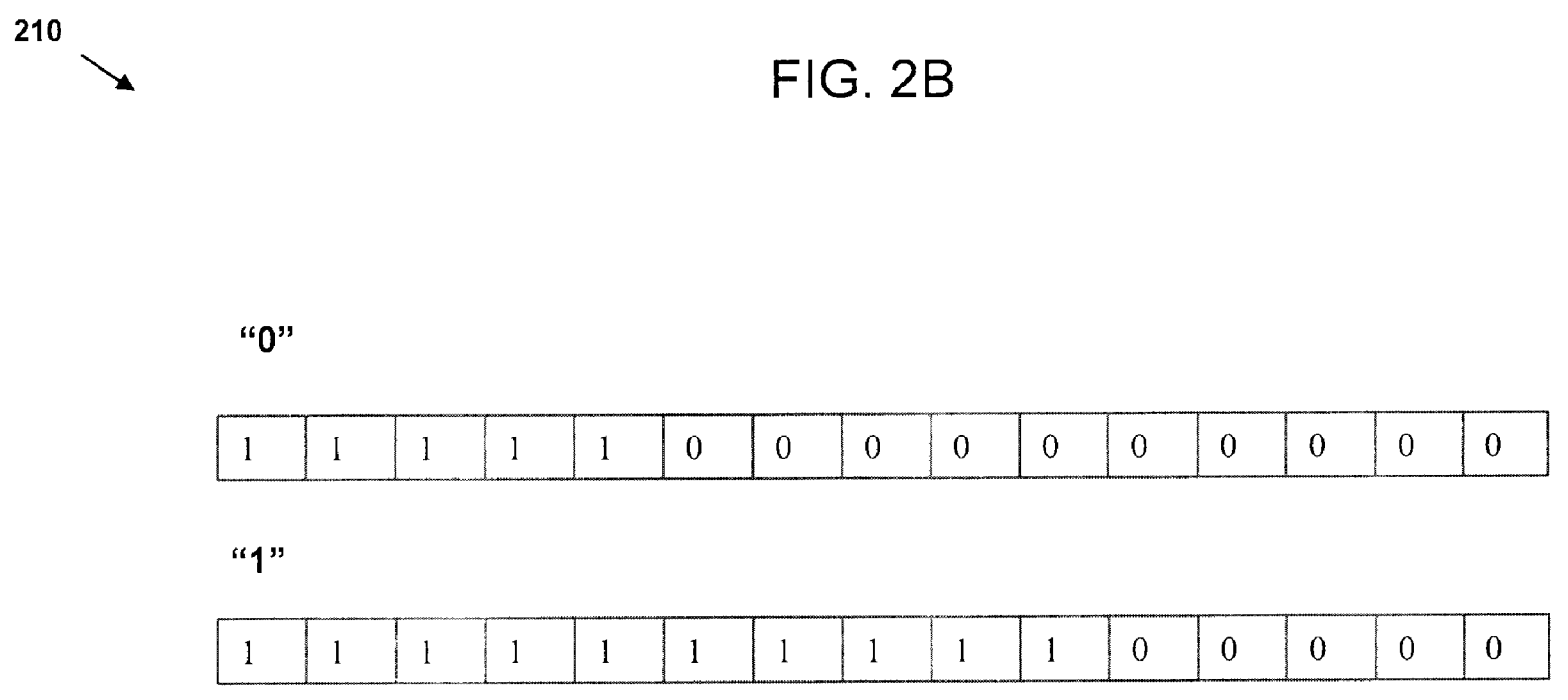

Referring now to FIG. 2B, depicted is one embodiment of a bit coding scheme 210 in which pulse width modulation with 15 radio frequency (RF) cycles are used. In one embodiment a "0" bit has 5 on-cycles and 10 off-cycles. Similarly, a "1" bit may have 10 on-cycles and 5 off-cycles. Redundant cycles may be included to tolerate up to 2-cycle errors. By way of example, Table 1 below shows one embodiment of a decoding scheme:

TABLE 1

| Decoding Scheme | |
| --- | --- |
| Error | on-cycle $\leq 2$ |
| "0" | $3 \leq$ on-cycle $\leq 7$ |
| "1" | $8 \leq$ on-cycle $\leq 12$ |
| Error | on-cycle $\geq 13$ |

In one embodiment, each bit must start with an on-cycle and end with an off-cycle. In this way, the start of a bit may be associated with a rising edge, which can be used as a clock signal to trigger other events in the implanted circuit.

Figure 3:
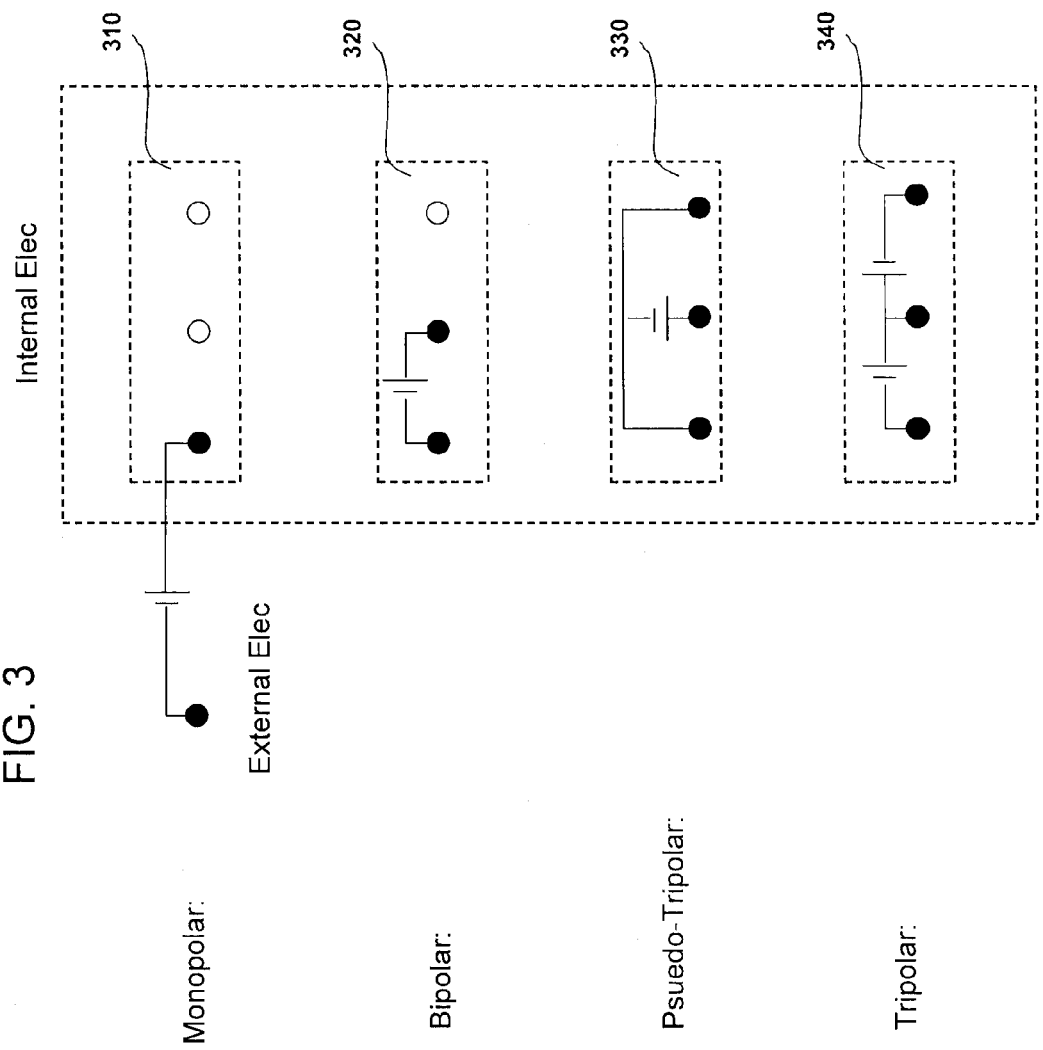
FIG. 3 depicts stimulation modes supported by the data encoding scheme of one embodiment of the invention.

In one embodiment, the flexible coding scheme of the invention may provide a high temporal resolution, with the shortest pulse duration being set to 8 μs and a temporal resolution set to one period of data bit (0.5 μs). This high temporal resolution may also allow accurate encoding of fundamental frequency (F0) and frequency modulated (FM) information.
Stimulation Mode Referring now to FIG. 3. depicted are at least some of the stimulation modes supported by the data encoding scheme of one embodiment of the invention. In particular, an internal electrode configuration 310 for a monopolar stimulation mode is shown. In addition, FIG. 3 further depicts an internal electrode configuration 320 for a bipolar stimulation mode, an internal electrode configuration 330 for a pseudo-tripolar stimulation mode, and an internal electrode configuration 340 for a tripolar stimulation mode. In this fashion, one embodiment of the invention may provide a flexible encoding scheme for a variety of stimulation modes.

Figure 4A:
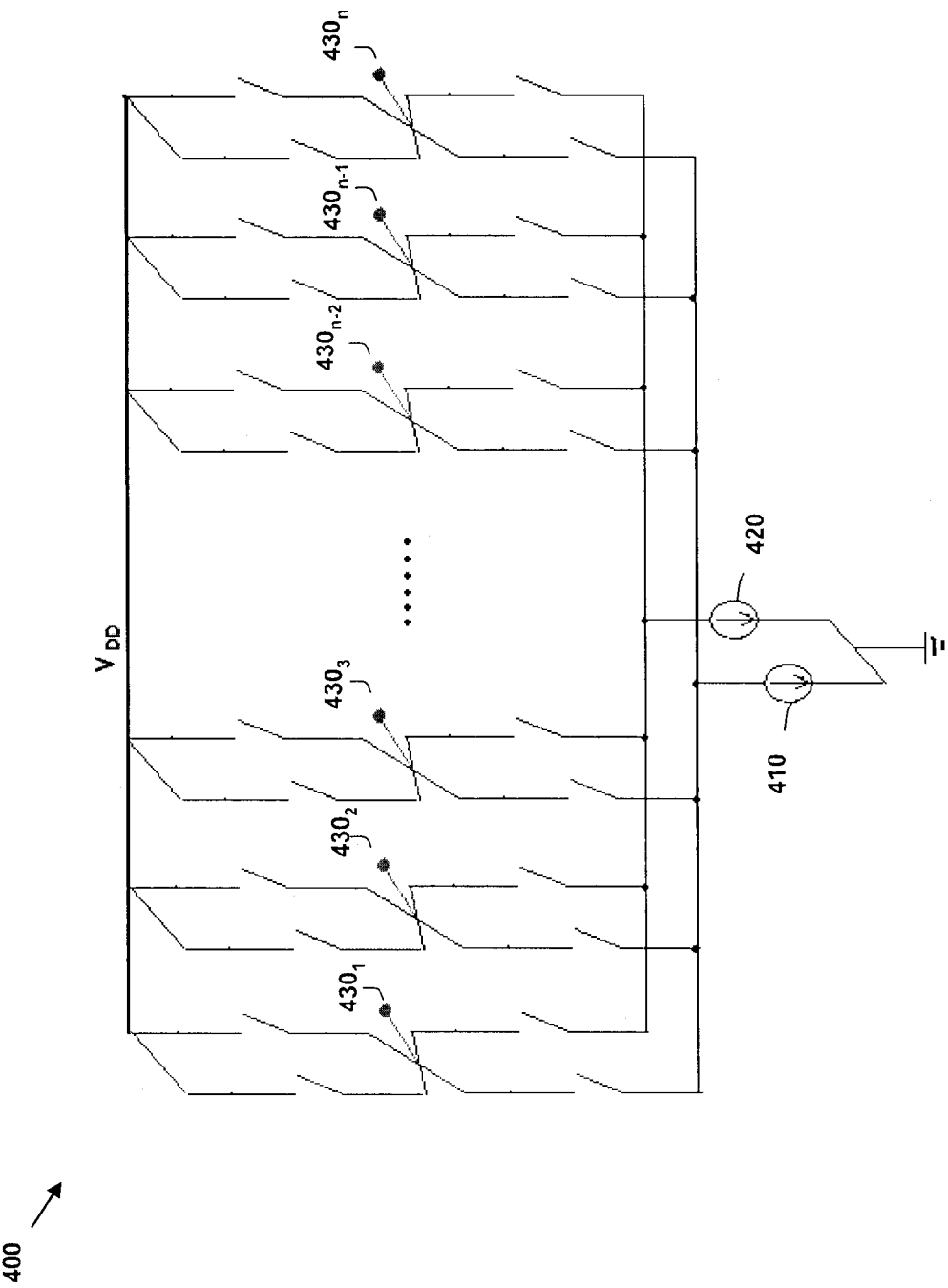
FIGS. 4A-4C depict embodiments of switch networks for various stimulation modes.
Figure 4B:
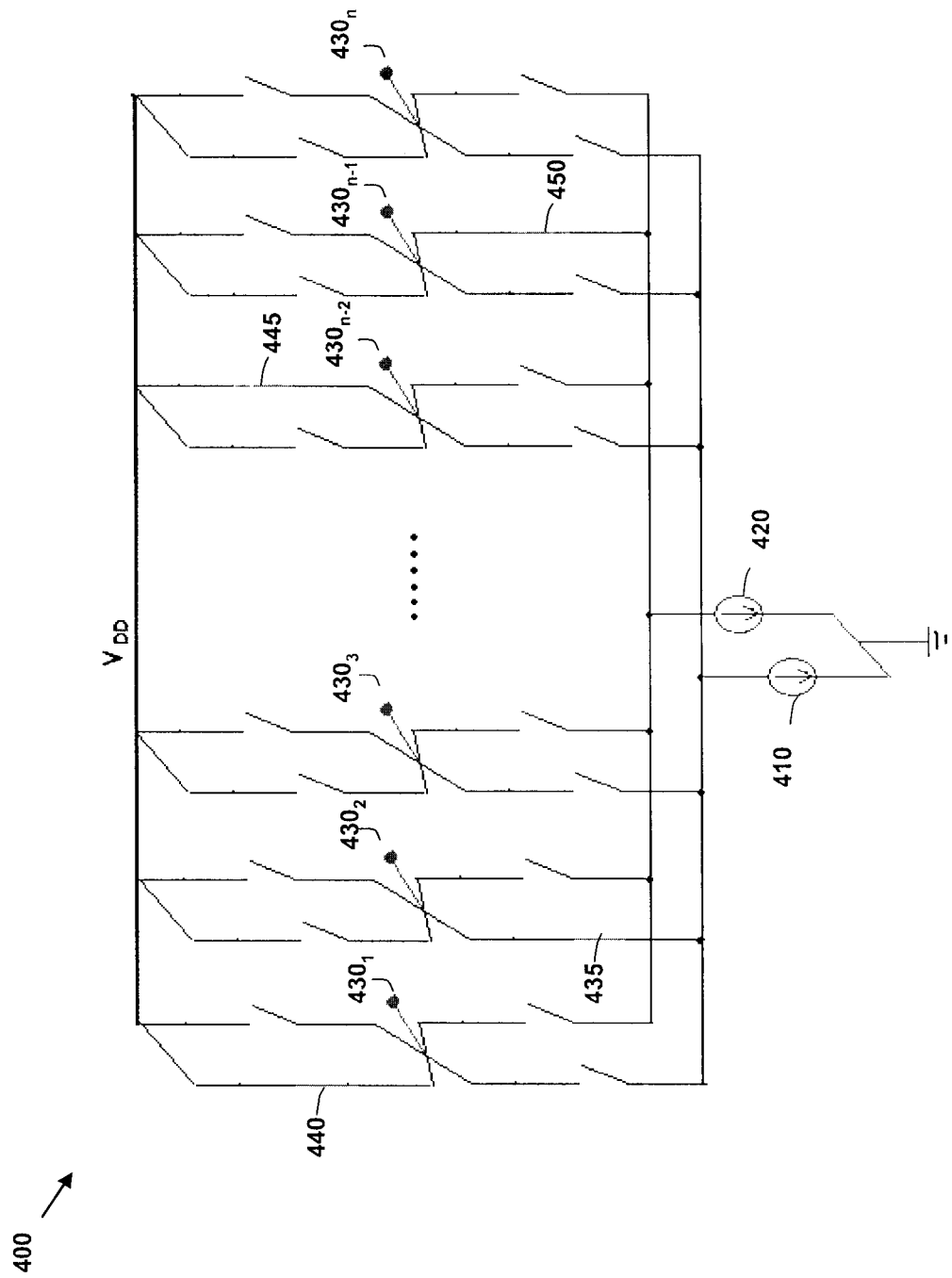
Figure 4C:
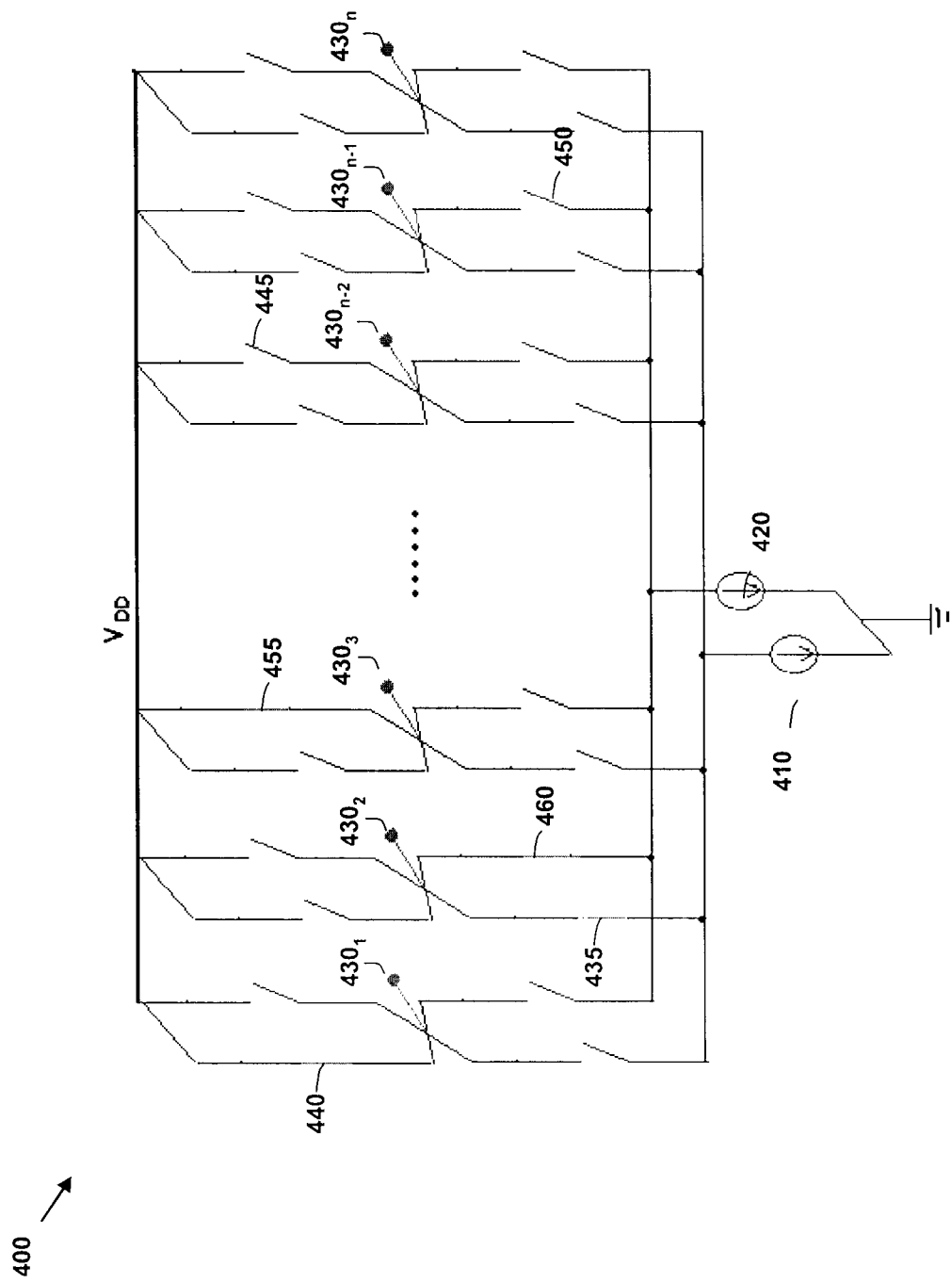

Referring now to FIGS. 4A-4C, depicted are exemplary switch networks for various stimulation modes, in accordance with the principles of the invention. As shown, a flexible coding scheme of the invention may allow high power and coding efficiency, while providing arbitrary waveform outputs, including alternating or consecutive monophasic pulses for power and electric stimulation efficiency. To that end, FIG. 4A depicts a switching network 400 comprising of a first current source 410 and a second current source 420, electrically connected to a plurality of electrodes $430_1$-$430_n$. As will be understood by one in the art, when one or more of the switches of switch network 400 are closed, a voltage $V_{DD}$ may be provided to stimulate one or more of the plurality of electrodes $430_1$-$430_n$.

FIG. 4B depicts the switching network 400 in which bipolar stimulation of the plurality of electrodes $430_1$-$430_n$ is being implemented using the first current source 410 and the second current source 420. As shown, switches 435, 440, 445 and 450 have been closed in order to implement bipolar stimulation. It should of course be understood that numerous other switching arrangements may be used in accordance with the invention.

Referring now to FIG. 4C, depicted is the switching network 400 implementing tripolar stimulation of the plurality of electrodes $430_1$-$430_n$ using the first current source 410 and the second current source 420. As shown, in addition to having switches 435 and 440 closed, switches 455 and 460 are also closed. In addition, switches 445 and 450 have been opened in order to implement the tripolar stimulation scheme. As with the embodiment of FIG. 4B, it should of course be understood that numerous other switching arrangements may be used in accordance with the invention.

In certain embodiments, the stimulation mode may be set in the command frame not in the data frame. As previously mentioned, four of the possible stimulation modes include bipolar, monopolar, pseudo-tripolar and tripolar.

Bipolar stimulation can be implemented by either using one current source multiplexing between different electrodes, or by using two current sources in a monopolar mode. By way of example, FIG. 5A depicts one embodiment of a command frame 500 for the bipolar mode at a first electrode (e.g., one of electrodes 130) using a first current source (e.g., current source $120_1$). Similarly, an exemplary data frame 510 is also depicted in FIG. 5A.

By way of providing another example of bipolar stimulation, FIG. 5B depicts another exemplary command frame 520 and corresponding data frame 530 for a first electrode, but in this case using two current sources (e.g., current source $120_1$ and current source $120_2$). In one embodiment, the polarity of the two current sources may be opposite in order to cancel out the electrode field outside of the two electrodes.

With respect to a monopolar stimulation mode, one embodiment of a command frame 540 and data frame 550 using one current source are depicted in FIG. 5C.

In the case of a Pseudo-tripolar stimulation mode, one embodiment of a command frame 560 and data frame 570 using one current source are depicted in FIG. 5D. In the pseudo-tripolar mode of FIG. 5D, only one current source may be used and the returning two electrodes may be grounded.

An exemplary command frame 580 and data frame 590 for a tripolar stimulation mode are shown in FIG. 5E. As shown, two current sources are used, and each returning electrode drain is half of the total current.

Finally, a special high-rate stimulation mode can be achieved using a high-rate mode command using a high rate data frame 595, as shown in the embodiment of FIG. 5F. Information regarding stimulation mode, pulse duration, gap duration, and current source may be transmitted before stimulation. In certain embodiments, only information regarding electrode, pulse polarity, and amplitude may be updated for cycle. Stimulation may start as soon as all 18 bits are transferred and decoded. The overall stimulation rate can be as high as 31-kHz with 1 current source and 62-kHz with 2 current sources.

Arbitrary Waveform Generation

Figure 6B:
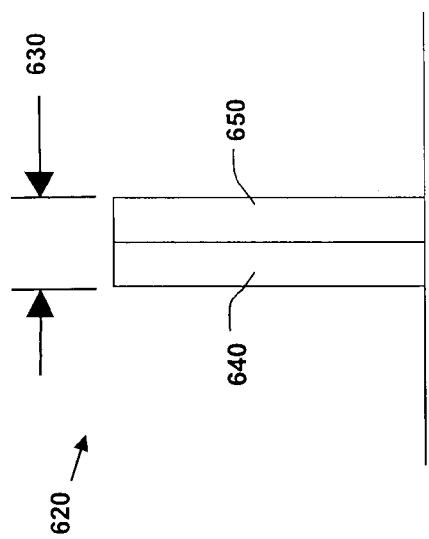
FIGS. 6A-6B depict an arbitrary waveform generator according to one embodiment of the invention.
Figure 6A:
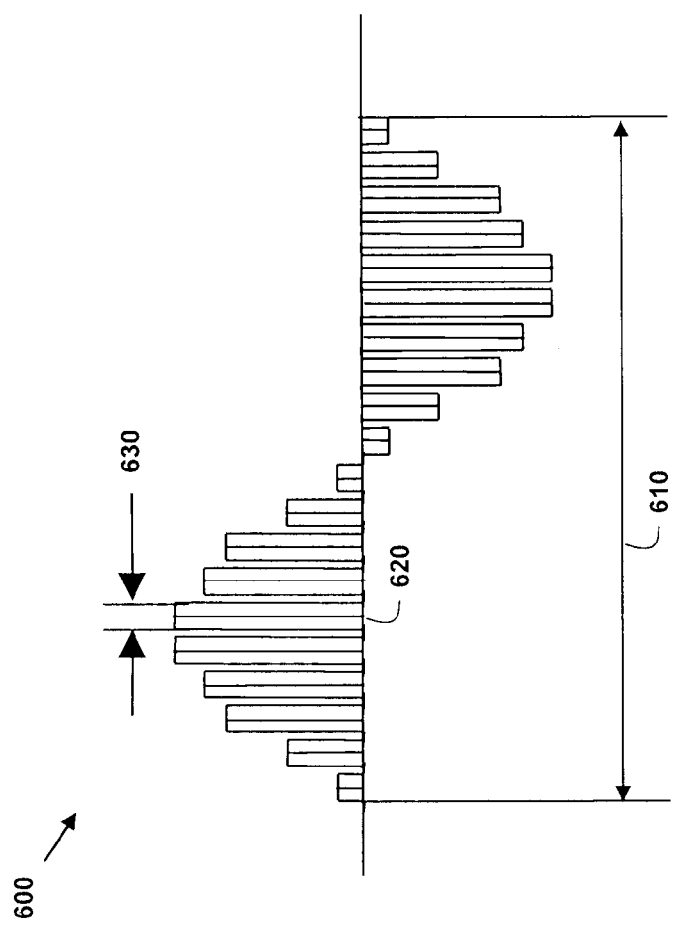

Referring now to FIGS. 6A-6B, depicted is an arbitrary waveform 600 generated using a flexible phase polarity, in accordance with one embodiment of the invention. As shown, each pulse comprises two phases thereby forming a bi-phasic period. The total charge for one period of the sinusoid 610 may be zero, meaning that the total charge is balanced. However, unlike the typical case, the polarity of each of the two phases of a pulse, such as pulse 620, may be arbitrarily assigned. This may allow for alternating phase pulses (negative-positive, positive-negative) and monolithic phase pulses (negative-negative, positive-positive), unlike prior art embodiments. This feature may be especially useful to generate pseudo-analog-waveform stimulations, where the biphasic pulses are not charge balanced for each individual pulse, but the accumulated long term charge is balanced over the entire sinusoid 610, as shown in FIG. 6A. In one embodiment, this is enabled using the previously-described two polarity bits for the two individual phases. While it should be appreciated that the sinusoid 610 may be longer or shorter, in one embodiment the sinusoid 610 may be approximately 100 µs, while the bi-phasic period 630 may be approximately 50 µs. Obviously, different values may assigned to each of the sinusoid 610 and/or period 630.

Referring now to FIG. 6B, depicted is an enlarged view of the bi-phasic period 620 of FIG. 6A. As shown, period 620 is comprised of a first phase 640 and a second phase 650 each having the same polarity, and thus the same charge over the entire period 630. The next period can be programmed to have two pulses with the same amplitude but the opposite polarity. In certain embodiments, this flexible coding may be used to produce mono-phasic or tri-phasic waveforms, which have the advantage of lower stimulation thresholds and possibly more focused electrical fields than biphasic waveform. Longer battery life and possibly better performance can be achieved.

Strategy Implementation

In the practice of programmable current source design, there has been two general approaches. The first approach, which is now largely obsolete, is to control the gate-source voltage to get variable drain-source current. This method, used by first generation cochlear implant products, required that each current source be calibrated due to the fact that the nonlinear $V_{GS}$–$I_{DS}$ relationship has a large variation among transistors.

The second approach for current source design is to use a linear combination of fixed value current sources to get a desired current value. Usually, a group of high precision fixed value currents is used as reference currents to generate output current values by current mirroring. The majority of current cochlear implant products use this type of current source.

For this type of current sources, to achieve a higher stimulating accuracy, a smaller step size ΔI of current increment is required, under a given current range [$I_{min}$, $I_{max}$]. Thus, more current amplitude bits B are needed to get a smaller step size, as shown below:

$$\Delta I = \frac{I_{max} - I_{min}}{2^B}$$

However, more amplitude bits B usually means more unit current sources. For example, B=8 requires 255 unit current sources, and B=10 requires 1023 unit current sources. For an integrated circuit implementation, it is undesirable to have so many current sources, since more chip space is required causing a parasitic effect.

Current Source Implementation

Consider the example of B=8, $I_{min}$=0, $I_{max}$=2 mA, where there are 256 current levels with a step size of 8 µA. For small stimulations near threshold level T, this step size may be too large such that the actual T level might fall between two current levels. For large stimulations near the MCL, this step size may be too small such that different current levels make no difference to patients, thus wasting limited current levels. Thus, it may be desirable to use a small step size for small currents to get accurate T levels, and a large step size for large currents for adequate sensational variation.

Figure 7:
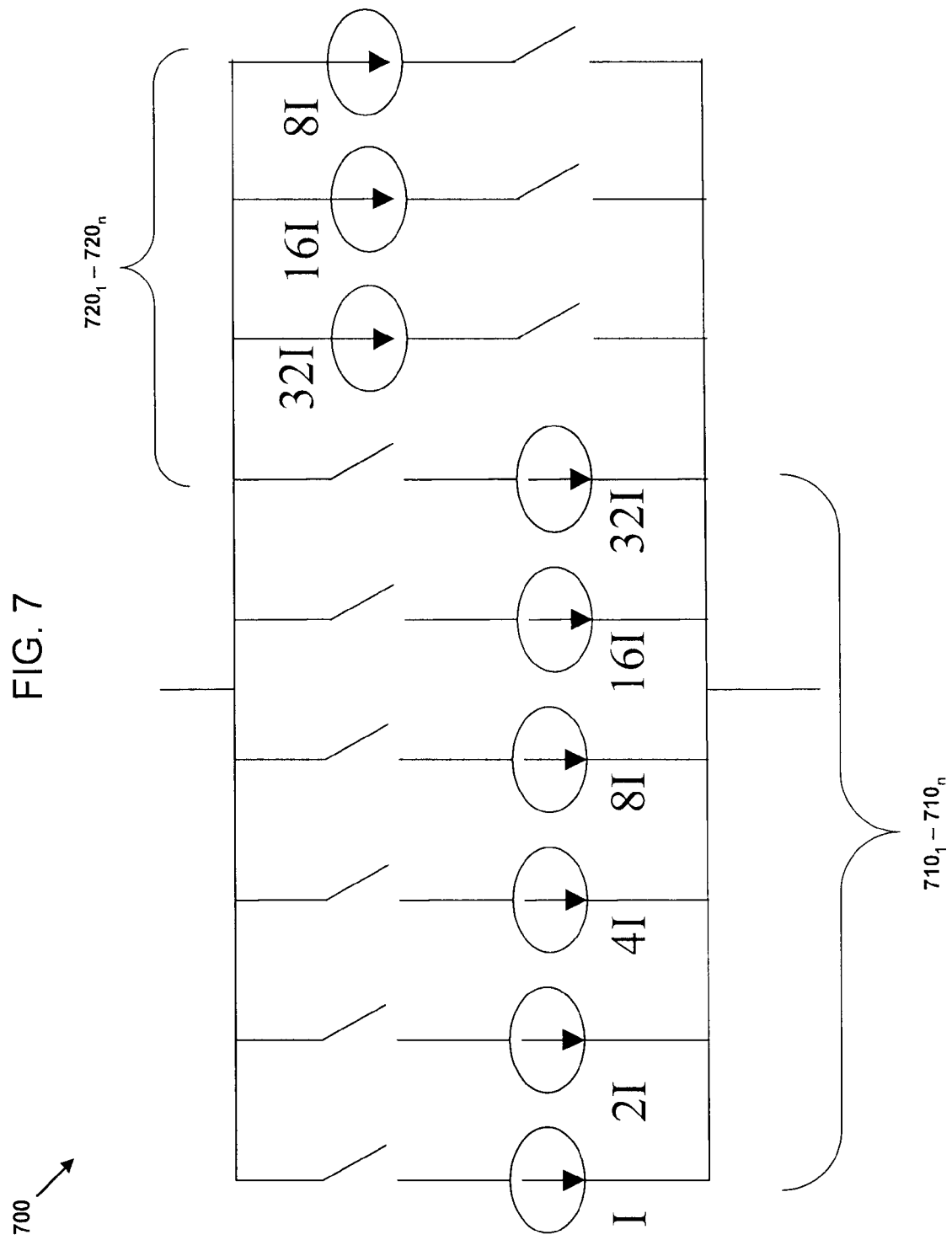
FIG. 7 illustrates one embodiment of a nonlinear step size current source implementation scheme.

One embodiment of a current source control scheme 700 in accordance with the principles of the invention is depicted in FIG. 7. In one embodiment, the current control scheme 700 supports nonlinear step-sizes for different current resolutions $710_1$-$710_n$, of I, 2I, 4I, 8I, 16I and 32I, for example, where I is the minimum reference current. In one embodiment, the amplitude may be encoded with a 6-bit value and the range with a 2-bit value, as described above with reference to FIG. 2. In one embodiment, an offset current circuit may be introduced. By way of a non-limiting example, the scheme 700 includes current sources $720_1$-$720_n$ usable to provide an offset current, and whose states may be controlled by the 2-bit range information.

Figure 8:
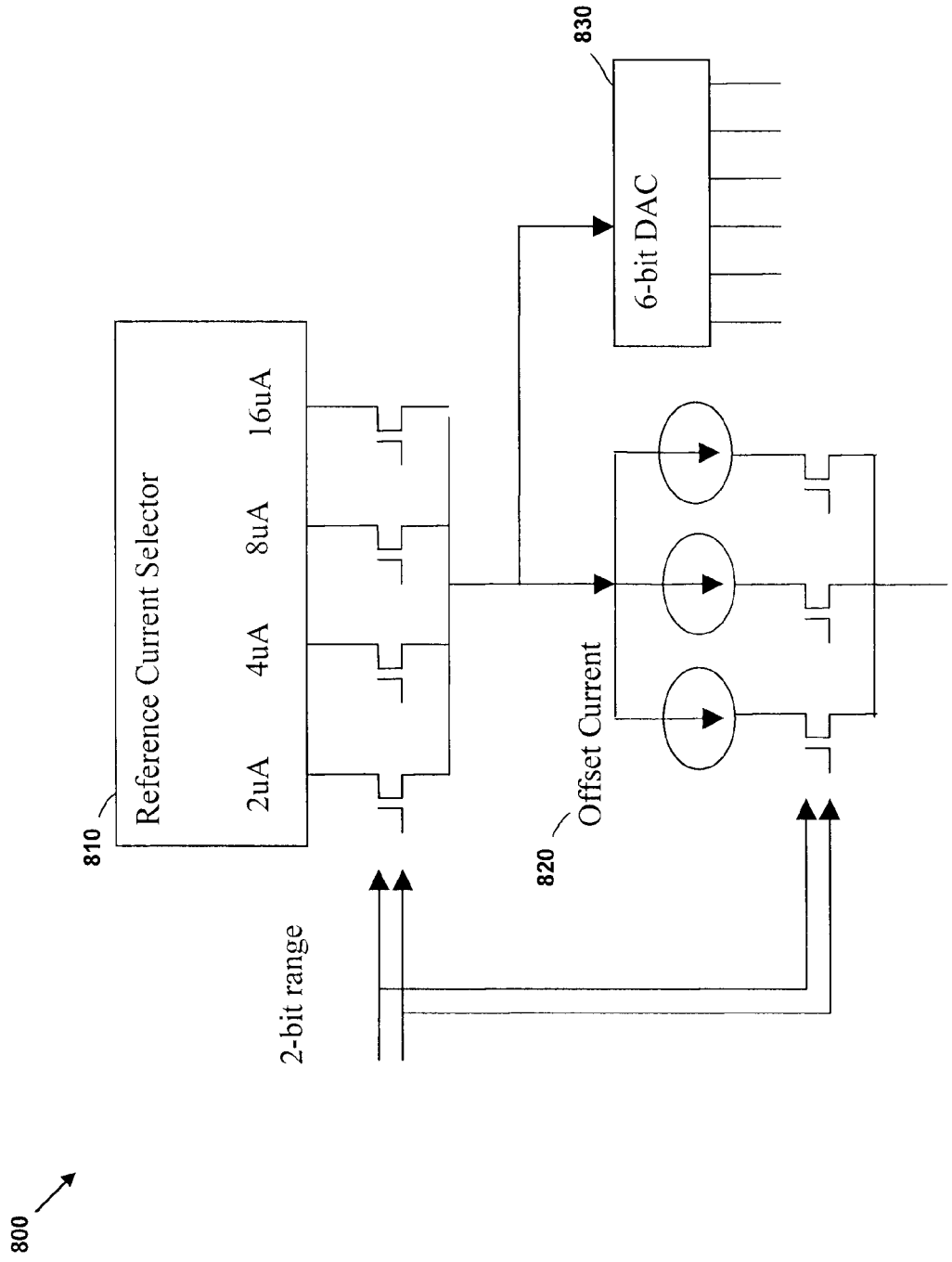
FIG. 8 shows one embodiment of a schematic for a reference current selection and offset current control circuit.

Referring now to FIG. 8, depicted is one embodiment of a control circuit 800 for reference current and offset current selection. In particular, reference current selector 810 decodes the 2-bit range to select one of four possible reference currents, (i.e., 2 µA, 4 µA, 8 µA and 16 µA). This information may then be used to control the offset current source 820, which in one embodiment is based on the selection of current sources $720_1$-$720_n$ from FIG. 7. In addition, the current selector 810 may further be configured to use the 6-bit amplitude information to control a 6-bit current digital-to-analog converter (DAC) 830. In one embodiment, the 6-bit DAC and the offset current source may use the same reference current I, in which case only one reference current generator may be needed. The following Table 2 depicts the exemplar bit controlled values for the control circuit 800:

TABLE 2

Exemplary Bit Controlled Current Values

| Range Bits | Reference Current | Offset Current | Minimum Current | Maximum Current |
|---|---|---|---|---|
| 00 | 2 µA | (0 + 0 + 0)*2 = 0 µA | 0 µA | 0 + (2⁶ − 1)*2 = 126 µA |
| 01 | 4 µA | (32 + 0 + 0)*4 = 128 µA | 128 µA | 128 + (2⁶ − 1)*4 = 380 µA |
| 10 | 8 µA | (32 + 16 + 0)*8 = 384 µA | 384 µA | 384 + (2⁶ − 1)*8 = 888 µA |
| 11 | 16 µA | (32 + 16 + 8)*16 = 896 µA | 896 µA | 896 + (2⁶ − 1)*16 = 1904 µA |

Table 2 above illustrates that for relatively small currents (e.g., 0-126 µA) the step size is 2 µA. For larger currents (896 µA-1904 µA), the step size is shown as being 16 µA. In the depicted embodiment, the current source uses 8 amplitude bits and a 6-bit DAC to achieve a minimal step size of a 10-bit DAC. Compared with 8-bit DAC, the 6-bit DAC uses 53% less unit current sources, and when compared with a 10-bit DAC, the 6-bit DAC uses 88% less unit current sources.

In certain embodiments, 8-bit 256 level nonlinear step size amplitude control may provide one or more of the following features:

Current precision improved: from 8 μA to 2 μA.
Same 8 amplitude bits, rather than 10 bits.
Uses 6-bit DAC rather than 10-bit DAC.
No command frame needed to set range.
Total number of unit current sources decreases from 255 (8-bit DAC) or 1023 (10-bit DAC) to 119.

Figure 9A:
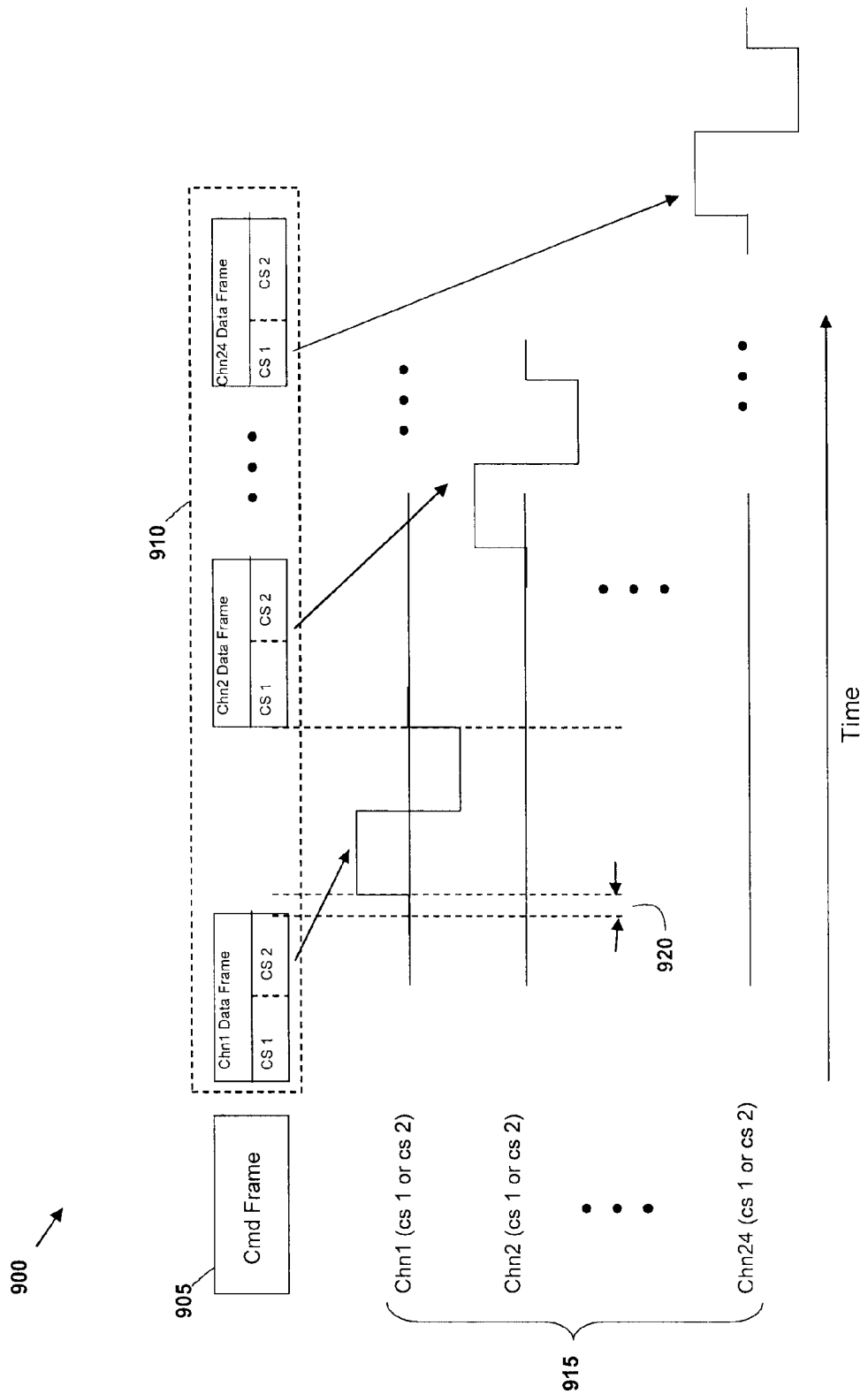
Figure 9B:
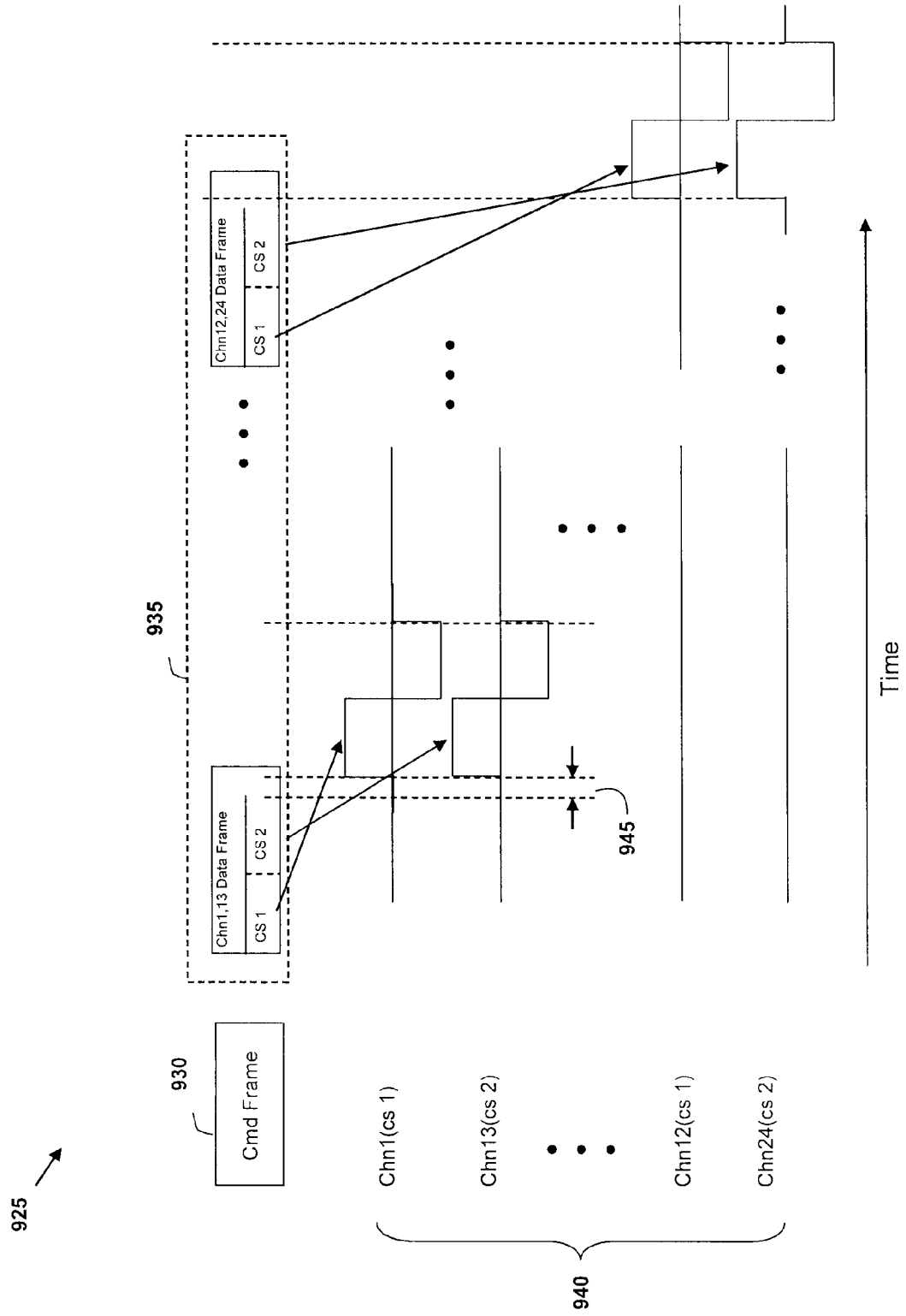

FIGS. 9A-9C depict various embodiments of CIS strategies in accordance with certain embodiments of the invention. In FIG. 9A, for example, a monopolar non-overlapping CIS strategy 900 is depicted. As shown, following command frame 905, data frames 910 are received for each of 24 possible channels for a two current source embodiment. In one embodiment, the data frame 910 may be configured in accordance with the embodiment of FIG. 2. In addition, each of the 24 possible channels may correspond to an individual electrode to be stimulated (e.g., electrodes 130 of FIG. 1).

Continuing to refer to FIG. 9A, the depicted Chn1 data frame is decoded to produce the corresponding pulse for Chn1 after delay 915 using either the first current source (cs1) or the second current source (cs2).

Similarly, the Chn2 data frame is decoded to produce the corresponding pulse for Chn2, as shown in FIG. 9A. It should be noted that the pulses for each of Chn1-Chn24 do not overlap since FIG. 9A corresponds to one embodiment of a monopolar non-overlapping CIS strategy. Moreover, each pulse of FIG. 9A further includes an amplitude encoded into the corresponding data frame, as described above, and may be generated using either current source.

FIG. 9B depicts one embodiment of an overlapping CIS strategy 925. As with the embodiment of FIG. 9A, a command frame 930 precedes data frames 935 for each of 24 possible channels 940, where each channel may correspond to an individual electrode to be stimulated (e.g., electrodes 130 of FIG. 1). However, unlike the non-overlapping CIS strategy 900, each data frames 935 of the overlapping CIS strategy 935 may include stimulation data for two channels—e.g., Chn1 and Chn13, Chn2 and Chn14, Chn3 and Chn15, etc. Thus, the depicted Chn1,13 data frame may be decoded to produce the pulse for Chn1 using cs1, as well as the pulse for Chn13 using cs2. In addition, these pulses may overlap, as shown in FIG. 9B. As with the embodiment of FIG. 9A, the embodiment of 9B includes delay 945 which is a result of the decoding process.

FIG. 9C illustrates another embodiment of a CIS strategy 950 in which two current sources are multiplexed to achieve simultaneous and non-simultaneous virtual channels. In one embodiment, the total number of virtual channels can be at least N+(N−1), where N equals the number of electrodes. In another embodiment, more virtual channels are possible if the amplitudes between two adjacent channels are manipulated.

While the invention has been described in connection with various embodiments, it should be understood that the invention is capable of further modifications. This application is intended to cover any variations, uses or adaptation of the invention following, in general, the principles of the invention, and including such departures from the present disclosure as come within the known and customary practice within the art to which the invention pertains.

What is claimed is:

1. A method for stimulating a plurality of electrodes implanted in a human inner ear comprising:
    multiplexing a plurality of current sources in accordance with a stimulation mode set using a command frame, wherein the plurality of current sources includes less then N current sources, where N is the number of electrodes in said plurality of electrodes;
    encoding stimulation data for the stimulation of the plurality of electrodes in a data frame following the command frame, wherein the stimulation data includes electrode address information, phase polarity information and amplitude information;
    generating a stimulation pulse based on said stimulation data and using one or more of the plurality of current sources in accordance with the stimulation mode, wherein at least one of the plurality of current sources is configured to produce a multi-resolution current based on a reference current; and
    delivering the stimulation pulse to one or more of the plurality of electrodes in accordance with the stimulation data.

2. The method of claim 1, wherein encoding comprises encoding stimulation data for two or more of the plurality of electrodes into a single data frame.

3. The method of claim 1, wherein the stimulation pulse begins and ends within a data frame, and wherein the stimulation data in the data frame further includes pulse width and inter-phase gap information.

4. The method of claim 3, wherein generating the stimulation pulse comprises generating the stimulation pulse using one or both of the pulse width and inter-phase gap information as a clock signal for timing control.

5. The method of claim 1, wherein the stimulation mode is a mode selected from the list consisting of: a monopolar stimulation mode, a bipolar stimulation mode and a pseudo-tripolar stimulation mode.

6. The method of claim 1, wherein multiplexing comprises multiplexing the plurality of current sources to achieve simultaneous and non-simultaneous virtual channels.

7. The method of claim 1, wherein the stimulation pulse comprises two phases, and wherein the phase polarity information comprises a polarity for each of the two phases, said polarity being the same for each of the two phases of the stimulation pulse.

8. The method of claim 7, a second phase of the stimulation pulse is connected to a first phase of a subsequent pulse to enable tri-phasic stimulation pulses.

9. The method of claim 1, wherein encoding the stimulation data comprises encoding the stimulation data in accordance with a continuous-interleaved-sampling strategy (CIS), wherein the CIS is selected from the group consisting of: a non-overlapping CIS, a high-rate CIS, an overlapping CIS and an alternating monophasic CIS.

10. The method of claim 1, wherein the plurality of current sources further comprises a plurality of offset current sources configured to produce a multi-resolution offset current based on the reference current.

11. The method of claim 1, wherein delivering the stimulation pulse comprises transmitting the stimulation pulse transcutaneously to the plurality of electrodes.

12. A programmable cochlear implant system comprising:
    a plurality of electrodes implanted in a human inner ear;
    a plurality of current sources multiplexed in accordance with a stimulation mode set using a command frame, wherein the plurality of current sources includes less then N current sources, where N is the number of electrodes in said plurality of electrodes; and
    a processing circuit including the plurality of current sources and electrically connected to the plurality of electrodes, the processing circuit configured to:
    encode stimulation data for the stimulation of the plurality of electrodes in a data frame following the command frame, wherein the stimulation data includes electrode address information, phase polarity information and amplitude information, generate a stimulation pulse based on said stimulation data and using one or more of the plurality of current sources in accordance with the stimulation mode, wherein at least one of the plurality of current sources is configured to produce a multi-resolution current based on a reference current, and deliver the stimulation pulse to one or more of the plurality of electrodes in accordance with the stimulation data.

13. The programmable cochlear implant system of claim 12, wherein the processing circuit is further configured to encode the stimulation data for two or more of the plurality of electrodes into a single data frame.

14. The programmable cochlear implant system of claim 12, wherein the stimulation pulse begins and ends within a data frame, and wherein the stimulation data in the data frame further includes pulse width and inter-phase gap information.

15. The programmable cochlear implant system of claim 14, wherein the processing circuit is further configured to generate the stimulation pulse by using one or both of the pulse width and inter-phase gap information as a clock signal for timing control.

16. The programmable cochlear implant system of claim 12, wherein the stimulation mode is a mode selected from the list consisting of: a monopolar stimulation mode, a bipolar stimulation mode and a pseudo-tripolar stimulation mode.

17. The programmable cochlear implant system of claim 12, wherein the plurality of current sources are multiplexed in accordance with the stimulation mode to achieve simultaneous and non-simultaneous virtual channels.

18. The programmable cochlear implant system of claim 12, wherein the stimulation pulse comprises two phases, and wherein the phase polarity information comprises a polarity for each of the two phases, said polarity being the same for each of the two phases of the stimulation pulse.

19. The programmable cochlear implant system of claim 18, a second phase of the stimulation pulse is connected to a first phase of a subsequent pulse to enable tri-phasic stimulation pulses.

20. The programmable cochlear implant system of claim 12, wherein the processing circuit is further configured to encode the stimulation data in accordance with a continuous-interleaved-sampling strategy (CIS), wherein the CIS is selected from the group consisting of: a non-overlapping CIS, a high-rate CIS, an overlapping CIS and an alternating monophasic CIS.

21. The programmable cochlear implant system of claim 12, wherein the plurality of current sources further comprises a plurality of offset current sources configured to produce a multi-resolution offset current based on the reference current.

22. The programmable cochlear implant system of claim 12, wherein the processing circuit is further configured to deliver the stimulation pulse by transmitting the stimulation pulse transcutaneously to the plurality of electrodes.

* * * * *